United States Patent [19]

Barry et al.

[11] Patent Number: 4,900,558
[45] Date of Patent: Feb. 13, 1990

[54] SUSTAINED RELEASE IBUPROFEN FORMULATION INCLUDING A CORE OF IBUPROFEN AND A MICROCRYSTALLINE CELLULOSE AND A COVERING OF ACRYLIC POLYMER AND HYDROXYLATED CELLULOSE DERIVATIVE

[75] Inventors: Brian W. Barry, Guiseley; Bryan A. Mulley, Bradford; Peter York, Ilkley, all of United Kingdom

[73] Assignee: APS Research Limited, Cleckheaton, United Kingdom

[21] Appl. No.: 79,206

[22] Filed: Jul. 30, 1987

[30] Foreign Application Priority Data

Aug. 1, 1986 [GB] United Kingdom ............... 8618811

[51] Int. Cl.$^4$ .................... A61K 9/16; A61K 9/24
[52] U.S. Cl. .................... 424/461; 424/462; 424/470; 424/494; 424/497
[58] Field of Search ............ 424/461, 462, 470, 494, 424/497

[56] References Cited

U.S. PATENT DOCUMENTS

| | | | |
|---|---|---|---|
| 4,138,475 | 2/1979 | McAinsh et al. | 424/456 |
| 4,205,060 | 5/1980 | Monsimer et al. | 424/497 |
| 4,343,789 | 8/1982 | Kawata et al. | 424/497 |
| 4,555,399 | 11/1985 | Hsigo | 424/497 |
| 4,578,264 | 3/1986 | Stricker et al. | 424/462 |
| 4,695,591 | 9/1987 | Hanna et al. | 424/499 |
| 4,710,384 | 12/1987 | Rotman | 424/470 |

OTHER PUBLICATIONS

A. T. Florence and D. Attwood, *Physicochemical Principles of Pharmacy*, pp. 319 to 324 (MacMillan 1988).
Edited by E. A. Rawlins, Bentley's Textbook of Pharmaceutics, Eighth Edition, pp. 661–62, Published by Bailliere Tindall, London (1977).

Primary Examiner—Mark L. Bell
Assistant Examiner—David M. Brunsman
Attorney, Agent, or Firm—Spencer & Frank

[57] ABSTRACT

The present invention provides a sustained release αmethyl-4-(2-methylpropyl)benzene acetic acid (Ibuprofen) formulation comprising sufficient granules to provide a predetermined dose or number of doses of Ibuprofen, each granule having a diameter between 0.5 and 2.0 mm and comprising:
 (a) a core containing 100 parts of Ibuprofen and from 10 to 70 parts of a microcrystalline cellulose; and
 (b) a coating covering substantially the whole surface of the core and comprising 100 parts of a water insoluble but water swellable acrylic polymer and 20 to 70 parts of a water-soluble hydroxylated cellulose derivative, the weight of the coating being from 5 to 20% of the weight of the core.

10 Claims, 2 Drawing Sheets

Blood level time profiles after a fourth day morning dose following three days of OSAT S/R Ibuprofen (600mg b.d.) and a standard formulation (Brufen 400mg t.i.d.)

Plasma levels following administration of Brufen (Ibuprofen 200mg). Mean of five subjects.

Plasma levels (±SEM) following administration of Fenbid (Ibuprofen 300mg). Mean of five subjects.

Plasma levels (±SEM) following administration of product 11 300mg. Mean of five subjects.

Blood level time profiles after a fourth day morning dose following three days of OSAT S/R Ibuprofen (600mg b.d.) and a standard formulation (Brufen 400mg t.i.d.)

SUSTAINED RELEASE IBUPROFEN FORMULATION INCLUDING A CORE OF IBUPROFEN AND A MICROCRYSTALLINE CELLULOSE AND A COVERING OF ACRYLIC POLYMER AND HYDROXYLATED CELLULOSE DERIVATIVE

The present invention relates to a sustained release Ibuprofen formulation, and in particular to such a formulation which will provide sustained release of the Ibuprofen over a period of about twelve hours.

It is well known that some medical conditions are best treated by administration of a pharmaceutical which is formulated to allow the pharmaceutical to act as quickly as possible. Such a formulation may comprise an injectable solution or a readily dissolvable tablet or capsule. Such formulations are useful, for instance, for treating acute pain, such as headaches or pain associated with trauma, such as an accident.

On the other hand some medical conditions are best treated by administration of a pharmaceutical in such a way as to sustain its action over an extended period of time. This type of administration is useful, for instance, for treating chronic pain, such as that associated with rheumatic or arthritic conditions.

This type of administration can be achieved by repeated administration of an immediate-release tablet or capsule at frequent intervals, for instance every four hours. However, this is generally inconvenient, especially during the night, when it is often necessary to wake a patient up to administer the tablet or capsule.

It has therefore been proposed to produce a formulation which will release the pharmaceutical therein at a controlled rate such that the amount of the pharmaceutical available in the body to treat the condition is maintained at a relatively constant level over an extended period. A particularly suitable period is twelve hours, since such a formulation need only be taken twice a day to maintain control of the condition. Such formulations are generally known as sustained release formulations.

Although many sustained release formulations are known, there is no generally applicable method by which such formulations can be designed. Each formulation is dependent on the particular pharmaceutical incorporated therein. In designing a formulation, it is generally necessary to take into account many factors, including the rates of absorbtion and clearance of the pharmaceutical, the interaction of the pharmaceutical with the excipients and/or coatings to be used in the formulation, the solubility of the excipients and/or coatings, and the effects on the bioavailability of the pharmaceutical which may be caused by the excipients and/or coatings. It is, however, not possible readily to predict whether any particular formulation will provide the desired sustained release, and it is generally found necessary to carry out considerable experimentation to produce a desired sustained release formulation.

It is known that Ibuprofen (which is the generic name for α-methyl-4-(2-methylpropyl)benzene acetic acid; see GB-A-0 971 700) is a pharmaceutical useful for the treatment of both acute and chronic pain. For instance, in the United Kingdom it is sold in an immediate release formulation as. (Brufen, Apsifen, Nurofen and Fenbid are all registered trade marks).

It has been found that the sustained release formulation which is on the market does not provide as good a sustained release over a twelve hour period as is desirable. There is therefore a need to provide an improved sustained release Ibuprofen formulation having good sustained release over a period of twelve hours. The present invention is based on the discovery of such an improved sustained release Ibuprofen formulation In the following description, all parts and percentages are by weight unless otherwise indicated.

According to the present invention, there is provided a sustained release Ibuprofen formulation comprising sufficient granules to provide a predetermined dose or number of doses of Ibuprofen, each granule having a diameter between 0.5 and 2.0 mm and comprising:

(a) a core containing 100 parts of Ibuprofen and from 10 to 70 parts of a microcrystalline cellulose; and (b) a coating covering substantially the whole surface of the core and comprising 100 parts of a water insoluble but water swellable acrylic polymer and 20 to 70 parts of a water-soluble hydroxylated cellulose derivative, the weight of the coating being from 5 to 20% of the weight of the core.

Preferably, the diameter of each granule is between 0.7 and 1.2 mm.

It will be appreciated that the exact diameter of the granules and the composition and amount of coating will depend on the time over which the formulation is designed to work.

For instance, for a 24 hour formulation, the granule diameter is preferably between 1.5 and 2.0 mm, the coating preferably contains 25 to 35 parts of the water soluble hydroxylated cellulose derivative, and the weight of the coating is approximately 20% of the weight of the core.

In another instance, for a 12 hour formulation, the granule diameter is between 0.7 and 1.2 mm, the coating preferably contains 25 to 35 parts of the water soluble hydroxylated cellulose derivative, and the weight of the coating is between 8 and 12% of the weight of the core.

The core preferably contains between 15 and 25 parts, advantageously 20 parts of the microcrystalline cellulose, and may conveniently be prepared by mixing the components together with some water to produce a slightly cohesive product. The cohesive product may then be extruded, chopped into suitable lengths, spheronised and dried.

Microcrystalline cellulose is a well known form of cellulose which is partially depolymerised. A particularly suitable microcrystalline cellulose is sold under the name Avicel TM (which is a registered trade mark). However, other equivalent materials may be used, as will be readily apparent to those skilled in the art.

Preferably, the coating comprises about 30 parts of the hydroxylated cellulose derivative. If too much of this derivative is present, the coating may become too sticky and the rate of release may become too high. If too little is present, the rate of release may be too low.

A particularly suitable hydroxylated cellulose derivative is hydroxypropyl methylcellulose having a degree of substitution of 28 to 30% of methoxy groups and 7 to 12% of hydroxy groups. However, other equivalent materials such as hydroxyethyl or hydroxymethyl celluloses can be used.

The acrylic polymer is preferably neutral and may comprise a homopolymer or a copolymer, for instance of acrylic acid esters or methacrylic acid esters. Preferably, the acrylic polymer is provided as an aqueous dispersion.

A particularly suitable acrylic polymer is sold under the name Eudragit TM (which is a registered trade mark), which comprises a copolymer of acrylic and methacrylic acid esters and which is usually supplied as an aqueous dispersion containing approximately 30% solids.

The coating may conveniently be prepared by forming a solution of the hydroxylated cellulose derivative and mixing it with a dispersion of the acrylic polymer. The aqueous mixture is then used to coat the dried core particles, and the coated particles are subsequently dried to produce the granules.

Preferably, the coated granules are sieved to ensure that they are in the correct size range.

The granules may be supplied loose with a means for dispensing a measured amount of granules, for instance to be sprinkled on food. Alternatively, the granules may be provided in sachets containing measured amounts.

The granules may, if desired, be formed into tablets using conventional tabletting machinery.

However, preferably the granules are placed in measured amounts in readily soluble capsules. The capsule may be any of those already known in the art, and may, for instance, comprise a thin gelatin skin. Preferably, the capsule contains either 200 or 300 mg of Ibuprofen.

It has surprisingly been found that by the above set out selection of the materials for the core and the coating, the relative amounts of the components, and the size of the granules, it has proved possible to produce a sustained release Ibuprofen formulation which acts effectively over any desired period, in particular a twelve hour period.

One embodiment of the present invention is now described, by way of example only, with reference to the accompanying drawings, in which.

EXAMPLE

Figure 1:
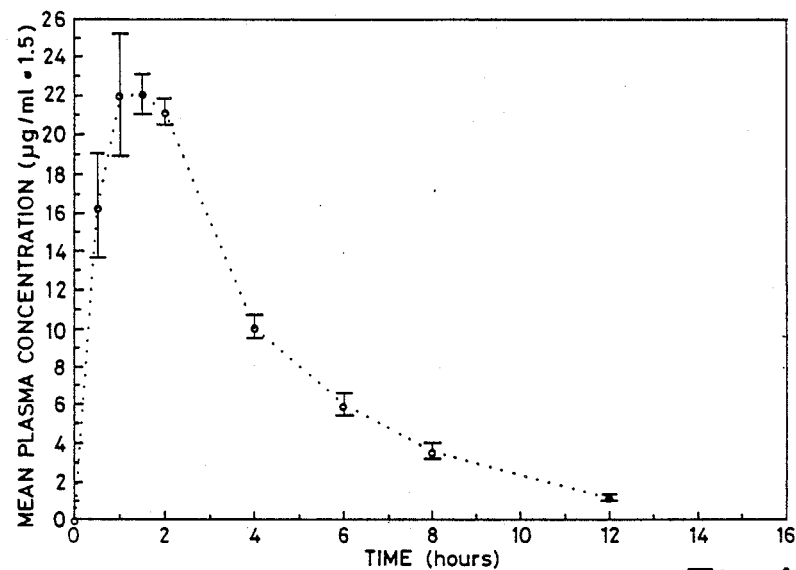
FIG. 1 shows the mean plasma concentration of Ibuprofen following administration of Brufen.

The formulation described below was developed using the OSAT system developed by the Inventors at the University of Bradford.

1000 g of Ibuprofen and 200 g of Avicel TM were mixed together by doubling up in a dry blender. 615 ml of water was added in portions until a slightly cohesive product was formed. The cohesive product was passed through an extruder and the extruded material was chopped to produce slugs having a diameter of about 1 mm and a length of 2 to 3 mm. The slugs were spheronised by passage through a spheroniser, and the particles thus formed were dried to a constant weight at 45° C. The dried particles were sieved to separate those having diameters between 0.7 and 1.5 mm.

15 g of hydroxypropyl methylcellulose was dissolved in 135 ml of hot water and cooled. The cooled solution was mixed with 167 g of Eudragit TM 30D (containing 50 g solids) and the mixture was diluted with a further 190 ml of water to produce a coating mixture containing 0.128 g solids per gram of mixture.

The sieved core particles were rotated in a small coating pan and the coating mixture was added in portions to the pan until the weight of solids in the added coating mixture was 10% of the weight of the core particles. After each portionwise addition of coating mixture, air was blown into the pan to assist in solvent removal. At the end of the addition of the coating mixture, the coated core particles were dried to constant weight at ambient temperature and sieved to produce granules having a size between 0.8 and 1.2 mm.

Hard gelatin capsules were each filled with 400 mg of the granules, to produce a total dose of 300 mg of Ibuprofen per capsule.

The following experiments were carried out on healthy human volunteers to determine the release properties of the formulation set out above in comparison to Brufen and Fenbid.

Each volunteer had a light evening meal and drank 1.5 l of tap water during the course of the evening prior to each trial For the trials with Brufen TM, which is an immediate release formulation, each volunteer had a light breakfast at 08.00 hrs and took an oral dose of 200 mg Brufen at 10.30 hrs. Blood samples were collected at 0.5, 1, 1.5, 2, 4, 6, 8 and 12 hours after administration of the dose.

For the trials with Fenbid TM and the formulation of the invention, each volunteer took an oral dose of 300 mg of Ibuprofen, either as Fenbid or as formulated above, at 07.30 hrs and then had a light breakfast at 09.00 hrs. Blood samples were collected at 0, 2, 4, 6, 8, 10, 12 and 15 hours after administration of the dose.

During all the trials, only light meals were taken and each volunteer was limited to a daily fluid intake of approximately 1.5 l of water.

A washout period of one week was allowed between each of the three series of trials.

Blood samples were collected, by finger tip puncture with a sterile blood lancet, into heparinized capillary collection tubes. Plasma was harvested by centrifugation and deep-frozen until assayed. Assays were carried out by high pressure liquid chromatography on a 250×4.6 mm reversed phase column packed with Partisil TM 10 ODS at ambient temperature, using a mobile phase of 50% acetonitrile/50% water at pH 3, using a solution of butyl-p-hydroxybenzoate as an internal standard.

Referring now to the Figures, it can be seen from FIG. 1 that the plasma level of Ibuprofen following administration of Brufen rises rapidly to a peak at about 2 hours and rapidly falls to a low level.

Figure 2:
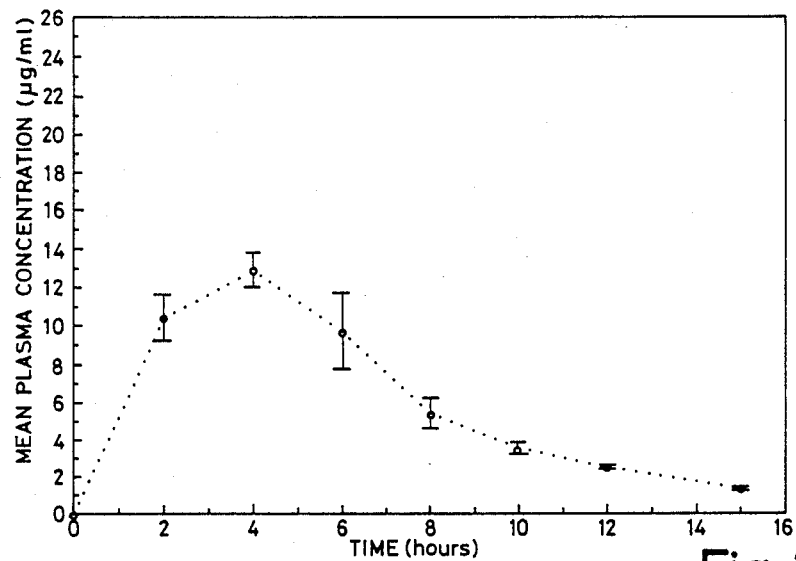
FIG. 2 is similar to FIG. 1, but relates to Fenbid.

From FIG. 2 it can be seen that for Fenbid the peak value occurs at approximately 4 hours with a less rapid rise and fall than for Brufen. However, the plasma level is by no means as constant as desirable.

Figure 3:
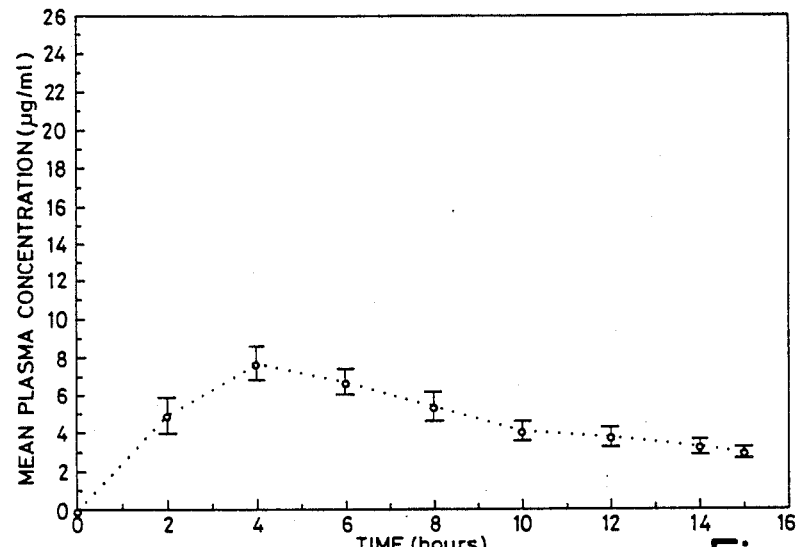
FIG. 3 is similar to FIG. 1, but relates to a formulation according to the present invention.

From FIG. 3 it can be seen that the plasma level obtained using the present formulation is much more constant than that obtained even with Fenbid, the level being relatively constant over a period of at least 2 to 12 hours following administration.

A measure of the sustained release properties of a formulation is the ratio between the plasma level at its peak and the plasma level at the end of the desired sustained release period, in this case 12 hours. This ratio preferably is as close to one as possible. For Brufen TM this ratio is 18.4, for Fenbid TM it is 5.3 and for the formulation of the present invention it is 2.1.

It can readily be seen from the data presented above that the present formulation provides a much improved twelve hour sustained release formulation than was previously available.

A further advantage of the present formulation is that it can be taken with or without food. If the formulation is taken with food, the time taken to reach its peak concentration in plasma is about the same as if it is taken without food, whereas the peak plasma concentration is slightly reduced and the absorbtion is spread over a slightly longer period. However, these differences are only minor and can for practical purposes be ignored, as the usual statistical tests did not show them to be significant.

Figure 4:
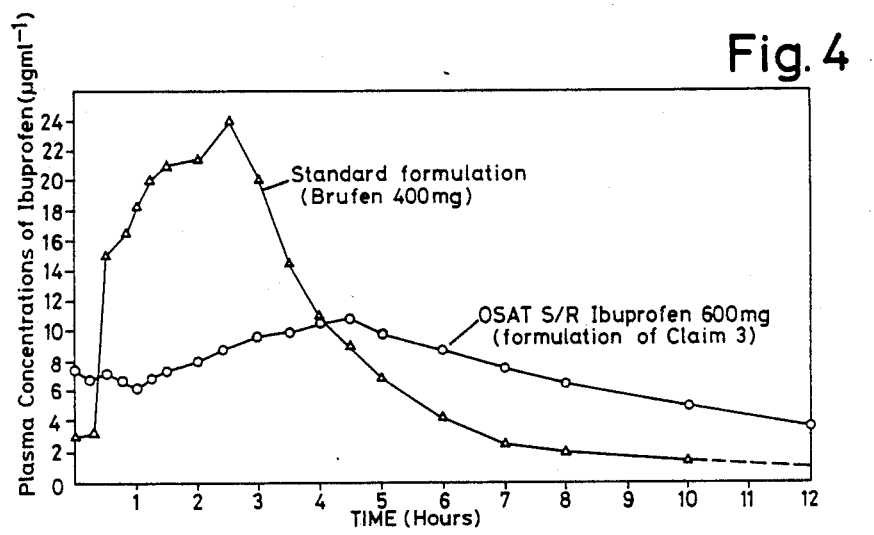
FIG. 4 shows blood level time profiles after a fourth day morning dose following three days of administration of a formulation according to the invention (—O—) and Brufen TM (—△—).

The present formulation has also been compared with the immediate-release formulation Brufen TM in a multi-dose, double-blind crossover study using 12 healthy human volunteers. FIG. 4 summarizes the results obtained. The study confirmed the pronounced sustained release characteristics of the present formulation and provided clear evidence of persisting drug levels in plasma in the morning following an evening dose, a phenomenon which is much less pronounced (and totally absent in some subjects) when Brufen is used. Therefore, the present formulation has the potential to relieve "morning stiffness", a common problem is rheumatic and arthritic patients. Also, the formulation has substantially no effect on the bioavailability of the Ibuprofen compared with the known immediate release formulations such as Brufen and Apsifen, although the apparent bioavailability of both was somewhat lower in the multi-dose study than in the single-dose studies.

Moreover, it has been shown that the formulation is storage stable over at least 12 months at high temperatures (up to 50° C.) and high relative humidity. There is little effect on the Ibuprofen or the sustained release properties under these stressful storage conditions and no effect under normal storage conditions.

It will be appreciated that the present invention has been described above by way of illustration only, and it will be clear that variations and alterations of detail may be made by the man skilled in the art without departing from the scope of the invention.

We claim:

1. A sustained release α-methyl-4-(2-methylpropyl)-benzene acetic acid (Ibuprofen) formulation comprising sufficient granules to provide a dose or number of doses of Ibuprofen, each granule having a diameter between 0.5 and 2.0 mm and comprising:

(a) a core containing 100 parts of Ibuprofen and from 10 to 70 parts of a microcrystalline cellulose; and
   (b) a coating covering substantially the whole surface of the core and comprising 100 parts of a water insoluble but water swellable acrylic polymer and 20 to 70 parts of a water-soluble hydroxylated cellulose derivative, the weight of the coating being from 5 to 20% of the weight of the core.

2. The formulation of claim 1, which is a 24 hour formulation, wherein the granule diameter is between 1.5 and 2.0 mm, the coating contains 25 to 35 parts of the water soluble hydroxylated cellulose derivative, and the weight of the coating is approximately 20% of the weight of the core.

3. The formulation of claim 1, which is a 12 hour formulation, wherein the granule diameter is between 0.7 and 1.2 mm, the coating contains 25 to 35 parts of the water soluble hydroxylated cellulose derivative, and the weight of the coating is between 8 and 12% of the weight of the core.

4. The formulation of claim 1, wherein the core contains between 15 and 20 parts of the microcrystalline cellulose.

5. The formulation of claim 1, wherein the coating comprises about 30 parts of the hydroxylated cellulose derivative.

6. The formulation of claim 1, wherein the hydroxylated cellulose derivative is hydroxypropyl methycellulose having a degree of substitution of 28 to 30% of methoxy groups and 7 to 12% of hydroxy groups.

7. The formulation of claim 1, wherein the acrylic polymer is neutral

8. The formulation of claim 1, wherein the granules are contained in a capsule.

9. A process for producing a formulation according to claim 1 comprising: 1. mixing the Ibuprofen with the microcrystalline cellulose; 2. forming the mixture into particles; 3. forming a solution of the hydroxylated cellulose derivative and the acrylic polymer and 4. coating the particles using the solution to form the granules.

10. The process of claim 9, wherein the granules are sieved after formation.

* * * * *